United States Patent
Leinweber et al.

(10) Patent No.: US 8,350,058 B2
(45) Date of Patent: Jan. 8, 2013

(54) METHOD FOR PRODUCING ALKENYL SUCCINIC ANHYDRIDES

(75) Inventors: Dirk Leinweber, Schwalbach (DE); Tobias Rau, Mainz (DE)

(73) Assignee: Clariant Produkte (Deutschland) GmbH, Frankfurt am Main (DE)

( * ) Notice: Subject to any disclaimer, the term of this patent is extended or adjusted under 35 U.S.C. 154(b) by 1218 days.

(21) Appl. No.: 11/793,431

(22) PCT Filed: Dec. 3, 2005

(86) PCT No.: PCT/EP2005/012967
§ 371 (c)(1),
(2), (4) Date: Jun. 15, 2007

(87) PCT Pub. No.: WO2006/066720
PCT Pub. Date: Jun. 29, 2006

(65) Prior Publication Data
US 2008/0108836 A1 May 8, 2008

(30) Foreign Application Priority Data
Dec. 15, 2004 (DE) .......................... 10 2004 060 295

(51) Int. Cl.
C07D 307/36 (2006.01)
C07D 307/34 (2006.01)
(52) U.S. Cl. ....................................... 549/255; 549/203
(58) Field of Classification Search .................. 549/203, 549/255
See application file for complete search history.

(56) References Cited

U.S. PATENT DOCUMENTS

| | | |
|---|---|---|
| 3,412,111 A | 11/1968 | Irwin |
| 3,476,774 A | 11/1969 | Zaweski |
| 4,691,030 A | 9/1987 | Fujino |
| 4,883,886 A | 11/1989 | Huang |
| 5,021,169 A | 6/1991 | Shin |

FOREIGN PATENT DOCUMENTS

| | | |
|---|---|---|
| DE | 3545133 | 6/1986 |
| WO | 9723474 | 7/1997 |

OTHER PUBLICATIONS

Mueller, E., "Methoden Der Organischen Chemie", 1975, Houben-Weyl, vol. IV/1b, Georg-Thieme-Verlag, Stuttgart, Germany, pp. 1059-1063 and 1094-1101.
International Search Report for PCT/EP2005/012967, mailed Mar. 16, 2006.
English Lang. Translation of International Preliminary Examination Report for PCT/EP2005/012967, mailed Nov. 28, 2007.
Klemchuck, PP, Antioxidants, Plastics, Additives, Ulmann's Encyclopedia of Industrial Chemistry, (Jun. 15, 2002).

*Primary Examiner* — Taylor Victor Oh
(74) *Attorney, Agent, or Firm* — Tod A. Waldrop

(57) ABSTRACT

The invention relates to a method for producing alkenyl succinic anhydrides of formula (1),

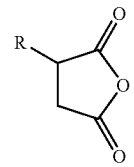

(1)

in which R represents a C4 to C250 alkylene radical that can be linear or branched. The method involves the reaction of maleic acid, maleic anhydride, fumaric acid or esters thereof and an alkene which contains 4-250 carbon atoms at from 150 to 250° C. in the presence of a synergistic mixture of a primary antioxidant, a secondary antioxidant, and a metal deactivator.

27 Claims, No Drawings

METHOD FOR PRODUCING ALKENYL SUCCINIC ANHYDRIDES

The present invention relates to a process for preparing alkenylsuccinic anhydrides, which is notable for higher conversions, higher purity of the reaction products and reduced formation of tarlike by-products, and to the use of the compounds prepared by this process.

Alkenylsuccinic anhydrides are used as starting materials for a multitude of chemical products, especially as the basis of emulsifiers, dispersants or lubricants.

Alkenylsuccinic anhydrides are prepared generally by reacting an alkene with maleic anhydride at temperatures of 150-250° C. in the so-called "ene reaction". As a result of the high thermal stress on the reactants during the reaction, the maleic anhydride on the one hand tends to decompose and the alkene used on the other hand tends to be oxidized or polymerized. As a result of these decomposition processes and side reactions, undesired insoluble tarlike by-products which have an adverse effect on the conversion and lead to highly colored, contaminated products form during the reaction.

The prior art already describes a multitude of chemical additives which are capable of suppressing the side reactions and decomposition reactions during the ene reaction.

U.S. Pat. No. 3,412,111 describes the synthesis of alkenylsuccinic anhydrides using antioxidants. Preference is given to hydroquinone, 2,2'-di(p-hydroxyphenyl)-propane and phenothiazines.

U.S. Pat. No. 3,476,774 describes sterically hindered substituted phenols which act as primary antioxidants during the preparation of alkenylsuccinic anhydrides. In particular, reference is made to the use of 4,4'-methylenebis(2,6-di-tert-butyl-phenol).

A further process for preparing polyalkenylsuccinic anhydrides is published in U.S. Pat. No. 4,883,886. In this process, the formation of by-products by 1,3-dibromo-5,5-dimethylhydantoin is suppressed.

Acidic or basic catalysts are used in DE-A-35 45 133 in order to obtain alkenyl-succinic anhydrides of high quality at low temperature in high yields. For example, titanium oxide, silicon oxide or aluminum oxide are effective here.

U.S. Pat. No. 5,021,169 describes a process for preparing alkenylsuccinic anhydrides in which products with reduced tarlike by-products and improved color are prepared by performing the ene reaction in the presence of a tri(orthoalkylphenyl)phosphite and optionally with additional use of a sterically hindered phenolic antioxidant. The use of metal deactivators is not described.

All processes for preparing alkenylsuccinic anhydrides which have already been described solve the problems of formation of tarlike by-products and the yields which are lowered as a result and the formation of highly colored products only partly. One reason for this is that the undesired side reactions, for example oxidation of alkene and/or maleic anhydride or polymerization of alkene and/or maleic anhydride proceed by very complex mechanisms which have not yet been clarified completely, which can be suppressed only to a limited degree by a single additive which is capable only of suppressing one of these side reactions.

It is thus an object of the invention to find an additive which, in the preparation of alkenylsuccinic anhydrides, leads to the substantial prevention of formation of tarlike decomposition products, high conversions and highly pure products. Surprisingly, this aim is achieved by the use of a synergistic additive mixture which consists of a primary antioxidant, a secondary antioxidant (peroxide decomposer) and a metal deactivator.

The invention therefore provides a process for preparing alkenylsuccinic anhydrides of the formula (1)

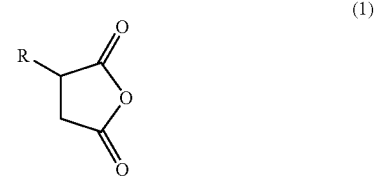

in which

R is a $C_4$- to $C_{250}$-alkylene radical which may be linear or branched, by reacting maleic anhydride and an alkene which contains 4-250 carbon atoms at from 150 to 250° C. in the presence of 0.001 to 1.0% of a synergistic mixture of a primary antioxidant, a peroxide decomposer and a metal deactivator.

The alkenylsuccinic anhydride thus obtained, and also the corresponding, inevitably formed bismaleated product, are formed by this process with high conversion, high purity and reduced formation of tarlike by-products.

The inventive preparation of alkenylsuccinic anhydrides with high conversion, high purity (low coloration) and reduced formation of tarlike by-products is in principle known in the prior art by reaction of an alkene with maleic anhydride at high temperatures (from 150 to 250° C.) at a reaction time of from 5 to 30 hours. For this purpose, it is also possible to use a high-boiling inert organic solvent. Instead of maleic anhydride, it is also possible to use maleic acid, fumaric acid or esters thereof for the process described. The compound which forms then differs from the compound specified in formula 1 by an acid or ester structure instead of the anhydride structure specified in formula 1.

The process according to the invention can be performed at standard pressure or at elevated pressure. A suitable alkene is preferably a high-reactive polyisobutene (content of terminal double bonds >85%) or a low-reactive polyisobutene (content of terminal double bonds <85%).

In order to prevent the oxidation of alkene or maleic anhydride by oxygen traces and the polymerization of the alkene or decomposition of the maleic anhydride induced by metal traces, for example iron or copper, in contrast to the prior art, not only one antioxidant is used as an inhibitor during the ene reaction but rather a synergistic mixture of a primary antioxidant, a secondary antioxidant (peroxide decomposer) and a metal deactivator. This allows all undesired side reactions to be substantially suppressed, which is manifested in high conversions, highly pure and low-color products and significantly reduced formation of tarlike by-products. The synergistic mixture of primary antioxidant, secondary antioxidant (peroxide decomposer) and metal deactivator is added to the reactant mixture of alkene and maleic anhydride in amounts of from 0.001 to 1.0 percent by weight (% by weight), preferably from 0.05 to 0.50% by weight and more preferably from 0.10 to 0.30% by weight.

The synergistic mixture comprises from 1 to 98% primary antioxidant, from 1 to 98% secondary antioxidant and from 1 to 98% metal deactivator, preferably from 10 to 80% antioxidant, from 10 to 80% peroxide decomposer and from 10 to 80% metal deactivator, more preferably from 20 to 40% antioxidant, from 20 to 40% peroxide decomposer and from 20 to 40% metal deactivator. In a further preferred embodiment, primary antioxidant, peroxide decomposer and metal deactivator add up to 100% by weight.

Suitable primary antioxidants, secondary antioxidants and metal deactivators are described as stabilizers for macromolecular substances in Houben-Weyl, Methoden der Organischen Chemie [Methods of organic chemistry], Volume 4/1b (Oxidationen II [Oxidations II]), p. 1049-1101, and in Ullmann's Encyclopedia of Industrial Chemistry "Antioxidants: Plastics, Additives".

Preferred primary antioxidants in the synergistic mixture are
1. Sterically hindered trialkylphenols, more preferably 2,6-di-tert-butyl-4-methylphenol, bis-(2-hydroxy-5-methyl-3-tert-butylphenyl)methane or 2,4,6-tristyrylphenol.
2. Hydroquinone derivatives, more preferably hydroquinone, 4-tert-butoxyphenol or 2,5-dihydroxy-1,4-di-tert-butylbenzene.
3. Aromatic amine derivatives, more preferably 1,4-bis(2-butylamino)benzene, 4-isopropylamino-1-phenylaminobenzene or 4-butylaminophenol.
4. Aromatic heterocycles, more preferably benzimidazole, 2-mercaptobenzimidazole or phenothiazine.

Preferred secondary antioxidants in the synergistic mixture are:
1. Trialkyl phosphites, for example tributyl phosphite, trihexyl phosphite or trioctyl phosphite.
2. Triaryl phosphites, for example tris(2,4-di-tert-butylphenyl)phosphite, tri(nonylphenyl)phosphites or triphenyl phosphite.
3. Sulfur compounds, especially thioethers or disulfides, more preferably distearyl 3,3'-thiodipropionate, distearyl disulfide or bis(dimethylaminothiocarbonyl) disulfide.

Preferred metal deactivators in the synergistic mixture are:
1. N,N'-Disalicylidene-1,2-diaminopropane, N,N'-disalicylidene-1,2-diaminoethane or N,N'-disalicylidene-1,2-diaminocyclohexane
2. Salicylic acid derivatives such as salicylic acid, acetylsalicylic acid or salicylic esters
3. Hydrazine derivatives such as diacylhydrazine, N,N'-bis(3-methoxy-2-naphthoyl)hydrazine, N,N'-bisacetyl(adipic hydrazide), N,N'-dibenzaloxalyl dihydrazide or 2',3-bis[3-(3,5-di-tert-butyl-4-hydroxyphenyl)propionyl]-propionohydrazide
4. Ethylenediamine-N,N,N',N'-tetraacetic acid (EDTA)
5. Tris[4,4'-thiobis(3-methyl-6-tert-butylphenol)]phosphite
6. Mannich-type reaction products formed from an alkylphenol, an aldehyde and a polyethylenepolyamine, more preferably from nonylphenol, formaldehyde and tetraethylenepentamine.

The advantage of the process according to the invention over the prior art processes will be illustrated hereinafter with reference to examples.

EXAMPLES

Example 1

Comparative

Reaction of Polyisobutene 950 and Maleic Anhydride (Without Inhibitor)

In a 1 liter four-neck flask, 475 g (0.50 mol) of polyisobutene 950 and 63.7 g (0.65 mol) of maleic anhydride were heated to 10° C. under a nitrogen atmosphere, and oxygen traces were removed by evacuating and purging with nitrogen three times with vigorous stirring.

The reaction mixture was then heated to 2000 C for 18 h, then excess maleic anhydride (10.0 g) was removed by distillation and the crude product was diluted with 170 g of mineral oil. Subsequently, the product was filtered through a pressure suction filter and the residue which had been filtered off was weighed (5.7 g of black tarlike decomposition products). The hydrolysis number of the dark brown cloudy product was 60 mg KOH/g, the residual olefin content 52% (mineral oil+unreacted polyisobutene).

Example 2

Comparative

Reaction of Polyisobutene 950 and Maleic Anhydride with 0.3% 2,6-di-tert-butyl-4-methylphenol (Primary Antioxidant, Prior Art)

In a 1 liter four-neck flask, 475 g (0.50 mol) of polyisobutene 950, 63.7 g (0.65 mol) of maleic anhydride and 1.6 g (0.3% by weight) of 2,6-di-tert-butyl-4-methylphenol were heated to 100° C. under a nitrogen atmosphere, and oxygen traces were removed by evacuating and purging with nitrogen three times with vigorous stirring.

The reaction mixture was then heated to 200° C. for 18 h, then excess maleic anhydride (6.2 g) was removed by distillation and the crude product was diluted with 170 g of mineral oil. Subsequently, the product was filtered through a pressure suction filter and the residue which had been filtered off was weighed (3.5 g of black tarlike decomposition products). The hydrolysis number of the dark brown cloudy product was 65 mg KOH/g, the residual olefin content 50% (mineral oil+unreacted polyisobutene).

Example 3

Comparison

Reaction of Polyisobutene 950 and Maleic Anhydride with 0.3% tri(2,4-di-tert-butylphenyl)phosphite (Secondary Antioxidant, Prior Art)

In a 1 liter four-neck flask, 475 g (0.50 mol) of polyisobutene 950, 63.7 g (0.65 mol) of maleic anhydride and 1.6 g (0.3% by weight) of tri(2,4-di-tert-butylphenyl)phosphite were heated to 100° C. under a nitrogen atmosphere, and oxygen traces were removed by evacuating and purging with nitrogen three times with vigorous stirring. The reaction mixture was then heated to 200° C. for 18 h, then excess maleic anhydride (7.9 g) was removed by distillation and the crude product was diluted with 170 g of mineral oil. Subsequently, the product was filtered through a pressure suction filter and the residue which had been filtered off was weighed (4.3 g of black tarlike decomposition products). The hydrolysis number of the dark brown cloudy product was 64 mg KOH/g, the residual olefin content 50% (mineral oil+unreacted polyisobutene).

Example 4

Reaction of Polyisobutene 950 and Maleic Anhydride with 0.15% 2,6-di-tert-butyl-4-methylphenol and 0.15% tri(2,4-di-tert-butylphenyl) Phosphite (Mixture of Prior Art Inhibitors)

In a 1 liter four-neck flask, 475 g (0.50 mol) of polyisobutene 950, 63.7 g (0.65 mol) of maleic anhydride and 0.8 g (0.15% by weight) of 2,6-di-tert-butyl-4-methylphenol and 0.8 g (0.15% by weight) of tri(2,4-di-tert-butylphenyl)phosphite were heated to 100° C. under a nitrogen atmosphere, and oxygen traces were removed by evacuating and purging with nitrogen three times with vigorous stirring.

The reaction mixture was then heated to 200° C. for 18 h, then excess maleic anhydride (6.8 g) was removed by distillation and the crude product was diluted with 170 g of mineral oil. Subsequently, the product was filtered through a pressure suction filter and the residue which had been filtered off was weighed (3.9 g of black tarlike decomposition products). The hydrolysis number of the dark brown cloudy product was 65 mg KOH/g, the residual olefin content 50% (mineral oil+ unreacted polyisobutene).

Example 5

Comparative

Reaction of Polyisobutene 950 and Maleic Anhydride with 0.3% N,N'-disalicylidene-1,2-diaminopropane (Metal Deactivator)

In a 1 liter four-neck flask, 475 g (0.50 mol) of polyisobutene 950, 63.7 g (0.65 mol) of maleic anhydride and 1.6 g (0.3% by weight) of N,N'-disalicylidene-1,2-diaminopropane were heated to 100° C. under a nitrogen atmosphere, and oxygen traces were removed by evacuating and purging with nitrogen three times with vigorous stirring.

The reaction mixture was then heated to 200° C. for 18 h, then excess maleic anhydride (8.2 g) was removed by distillation and the crude product was diluted with 170 g of mineral oil. Subsequently, the product was filtered through a pressure suction filter and the residue which had been filtered off was weighed (5.9 g of black tarlike decomposition products). The hydrolysis number of the dark brown cloudy product was 63 mg KOH/g, the residual olefin content 51% (mineral oil+ unreacted polyisobutene).

Example 6

Reaction of Polyisobutene 950 and Maleic Anhydride with a Synergistic Mixture of 0.1% 2,6-di-tert-butyl-4-methylphenol, 0.1% distearyl 3,3'-thiodipropionate and 0.05% N,N'-disalicylidene-1,2-diaminopropane In a 1 liter four-neck flask, 475 g (0.50 mol) of polyisobutene 950, 63.7 g (0.65 mol) of maleic anhydride and 0.54 g (0.1% by weight) of 2,6-di-tert-butyl-4-methylphenol, 0.54 g (0.1% by weight) of distearyl 3,3'-thiodipropionate and 0.27 g (0.05% by weight) of N,N'-disalicylidene-1,2-diaminopropane were heated to 100° C. under a nitrogen atmosphere, and oxygen traces were removed by evacuating and purging with nitrogen three times with vigorous stirring. The reaction mixture was then heated to 200° C. for 18 h, then excess maleic anhydride (4.4 g) was removed by distillation and the crude product was diluted with 170 g of mineral oil. Subsequently, the product was filtered through a pressure suction filter and the residue which had been filtered off was weighed (0.8 g of black tarlike decomposition products). The hydrolysis number of the clear bright yellow product was 72 mg KOH/g, the residual olefin content 46% (mineral oil+ unreacted polyisobutene).

Example 7

Comparative

Reaction of Dodecene and Maleic Anhydride with 0.15% 2,6-di-tert-butyl-4-methylphenol and 0.15% tri(2,4-di-tert-butylphenyl)phosphite (Mixture of Prior Art Inhibitors)

In an autoclave, 1260 g (7.5 mol) of dodecene, 490 g (5.0 mol) of maleic anhydride and 2.6 g (0.15% by weight) of 2,6-di-tert-butyl-4-methylphenol and 2.6 g (0.15% by weight) of tri(2,4-di-tert-butylphenyl)phosphite were heated to 100° C. under a nitrogen atmosphere, and oxygen traces were removed by evacuating and purging with nitrogen three times with vigorous stirring.

The reaction mixture was then heated to 220° C. for 6 h and then unconverted dodecene and maleic anhydride were removed by distillation. Subsequently, the product was filtered through a pressure suction filter and the residue which had been filtered off was weighed (85 g of black tarlike decomposition products). The hydrolysis number of the brownish product was 395 mg KOH/g.

Example 8

Reaction of Dodecene and Maleic Anhydride with 0.1% 2,6-di-tert-butyl-4-methylphenol, 0.1% distearyl 3,3'-thiodipropionate and 0.05% N,N'-disalicylidene-1,2-diaminopropane In an autoclave, 1260 g (7.5 mol) of dodecene, 490 g (5.0 mol) of maleic anhydride and 1.7 g (0.1% by weight) of 2,6-di-tert-butyl-4-methylphenol and 1.7 g (0.1% by weight) of distearyl 3,3'-thiodipropionate and 0.85 g (0.05% by weight) of N,N'-disalicylidene-1,2-diaminopropane were heated to 100° C. under a nitrogen atmosphere, and oxygen traces were removed by evacuating and purging with nitrogen three times with vigorous stirring.

The reaction mixture was then heated to 220° C. for 6 h and then unconverted dodecene and maleic anhydride were removed by distillation. Subsequently, the product was filtered through a pressure suction filter and the residue which had been filtered off was weighed (7.5 g of black tarlike decomposition products). The hydrolysis product of the bright yellow product was 420 mg KOH/g.

The examples adduced (table 1) show clearly that the synergistic blend of primary antioxidant, secondary antioxidant and metal deactivator (example 6) is far superior to the prior art additives. Example 4 additionally demonstrates that a two-component mixture of prior art additives is clearly inferior to the inventive synergistic blend. Without the presence of a metal deactivator, the conversions and the amount of undesired tarlike by-products increase. Example 5 also shows that a metal deactivator alone is not capable of suppressing the side reactions.

TABLE 1

| Product from example | HN [mg KOH/g] | Residual olefin content [%] | tarlike by-product [g] | unreacted MA [g] | Appearance |
|---|---|---|---|---|---|
| 1 | 60 | 52 | 5.7 | 10 | Dark brown cloudy |
| 2 | 65 | 50 | 3.5 | 6.2 | Dark brown cloudy |

TABLE 1-continued

| Product from example | HN [mg KOH/g] | Residual olefin content [%] | tarlike by-product [g] | unreacted MA [g] | Appearance |
|---|---|---|---|---|---|
| 3 | 64 | 50 | 4.3 | 7.9 | Dark brown cloudy |
| 4 | 65 | 50 | 3.9 | 6.8 | Dark brown cloudy |
| 5 | 63 | 51 | 5.9 | 8.2 | Dark brown cloudy |
| 6 | 72 | 46 | 0.8 | 4.4 | Bright yellow clear |

Examples 7 and 8 were not included in table 1 since, unlike examples 1 to 6, they do not relate to polyisobutenylsuccinic anhydrides but rather to dodecenylsuccinic anhydrides.

The invention claimed is:

1. A process for preparing an alkenylsuccinic anhydride of

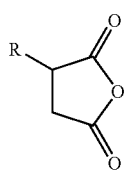

(1)

wherein

R is a $C_4$- to $C_{250}$-alkylene radical which may be linear or branched, comprising the step of reacting in an ene reaction a first component selected from the group consisting of maleic acid, maleic anhydride, fumaric acid and esters thereof with an alkene having 4-250 carbon atoms at a temperature from 150 to 250° C. in the presence of a synergistic mixture, wherein the synergistic mixture comprises a primary antioxidant, a secondary antioxidant and a metal deactivator.

2. The process as claimed in claim 1, wherein the alkene is selected from the group consisting of tripropylene, tetrapropylene, pentapropylene, and a $C_{8-30}$-α-olefin.

3. The process as claimed in claim 1, wherein the alkene is a polyisobutene of a molar mass, wherein the molar mass is selected from the group consisting of 550, 950, 1000, 1300, 2300, and mixtures thereof.

4. The process of claim 1, wherein the synergistic mixture of a primary antioxidant, a secondary antioxidant and a metal deactivator is used in an amount of from 0.001 to 1.0% by weight of the first component.

5. The process of claim 1, wherein the synergistic mixture consists of from 1 to 98% of a primary antioxidant, from 1 to 98% of a secondary antioxidant and from 1 to 98% of a metal deactivator.

6. The process of claim 1, wherein the primary antioxidant is a sterically hindered trialkylphenol selected from the group consisting of 2,6-di-tert-butyl-4-methylphenol, bis(2-hydroxy-5-methyl-3-tert-butylphenyl)methane, 2,4,6-tristyrylphenol and mixtures thereof.

7. The process of claim 1, wherein the primary antioxidant is selected from the group consisting of hydroquinone, 4-tert-butoxyphenol, 2,5-dihydroxy-1,4-di-tert-butylbenzene and mixtures thereof.

8. The process of claim 1, wherein the primary antioxidant is selected from the group consisting of 1,4-bis(2-butylamino)benzene, 4-isopropylamino-1-phenylaminobenzene, 4-butylaminophenol and mixtures thereof.

9. The process of claim 1, wherein the primary antioxidant is an aromatic heterocycle selected from the group consisting of benzimidazole, 2-mercaptobenzimidazole, phenothiazine and mixtures thereof.

10. The process of claim 1, wherein the secondary antioxidant is a trialkyl phosphite selected from the group consisting of tributyl phosphite, trihexyl phosphate, trioctyl phosphate and mixtures thereof.

11. The process of claim 1, wherein the secondary antioxidant is a triaryl phosphite selected from the group consisting of tris(2,4-di-tert-butylphenyl) phosphite, tri(nonylphenyl) phosphite, triphenyl phosphate and mixtures thereof.

12. The process of claim 1, wherein the secondary antioxidant is a sulfur compound selected from the group consisting of distearyl 3,3'-thiodipropionate, distearyl disulfide, bis(dimethylaminothiocarbonyl) disulfide and mixtures thereof.

13. The process of claim 1, wherein the metal deactivator is selected from the group consisting of N,N'-disalicylidene-1,2-diaminopropane, N,N'-disalicylidene-1,2-diaminoethane, N,N'-disalicylidene-1,2-diaminocyclohexane and mixtures thereof.

14. The process of claim 1, wherein the metal deactivator is selected from the group consisting of salicylic acid, acetylsalicylic acid, salicylic esters and mixtures thereof.

15. The process of claim 1, wherein the metal deactivator is selected from the group consisting of diacylhydrazine, N,N'-bis(3-methoxy-2-naphthoyl)hydrazine, N,N'-bisacetyl(adipic hydrazide), N,N'-dibenzaloxalyl dihydrazide, 2',3-bis[3-(3,5-di-tert-butyl-4-hydroxyphenyl)propionyl] propionohydrazide and mixtures thereof.

16. The process of claim 1, wherein the metal deactivator used in the synergistic mixture is ethylenediamine-N,N,N',N'-tetraacetic acid (EDTA).

17. The process of claim 1, wherein the metal deactivator used in the synergistic mixture is tris[4,4'-thiobis(3-methyl-6-tert-butylphenol)]phosphite.

18. The process of claim 1, wherein the metal deactivator used in the synergistic mixture is a Mannich reaction product formed from an alkylphenol, an aldehyde and a polyethylenepolyamine.

19. The process of claim 1, wherein the synergistic mixture consists of a primary antioxidant mixture and a secondary antioxidant mixture and a metal deactivator mixture.

20. The process of claim 1, wherein the process is performed under elevated pressure.

21. The process of claim 1, wherein the alkene and the first component are present in a molar ratio of from 1:0.5 to 1:3.

22. The process of claim 1, wherein the ene reaction is performed in a high-boiling inert organic solvent.

23. The process of claim 1, wherein the alkene is a high-reactive or low-reactive polyisobutene or a mixture thereof.

24. The process of claim 1, wherein the metal deactivator is a Mannich reaction product formed from nonylphenol, formaldehyde and tetraethylenepentamine.

25. The process of claim 1, wherein the primary antioxidant is selected from the group consisting of a sterically hindered trialkyl-phenol, hydroquinone, 4-tert-butoxyphenol, 2,5-dihydroxy-1,4-di-tert-butylbenzene, 1,4-bis(2-butylamino)benzene, 4-isopropylamino-1-phenylaminobenzene, 4-butylaminophenol benzimidazole, 2-mercaptobenzimidazole, phenothiazine and mixtures thereof.

26. The process of claim 1, wherein the secondary antioxidant is selected from the group consisting of a trialkyl phosphate, a triaryl phosphate, a thioether, a disulfide, distearyl 3,3'-thiodipropionate, a distearyl disulfide, bis(dimethylaminothiocarbonyl) disulfide, and mixtures thereof.

27. The process of claim 1, wherein the metal deactivator is a compound selected from the group consisting of salicylic acid, acetylsalicylic acid, salicylic esters and mixtures thereof.

* * * * *